(12) United States Patent
Fiere et al.

(10) Patent No.: US 9,034,037 B2
(45) Date of Patent: May 19, 2015

(54) VERTEBRAL OSTEOSYNTHESIS EQUIPMENT

(75) Inventors: Vincent Fiere, Collonges Au Mont d'Or (FR); Pierre Bernard, Merignac (FR); Olivier Ricart, Payrisch (LU)

(73) Assignee: MEDICREA INTERNATIONAL, Neyron (FR)

( * ) Notice: Subject to any disclaimer, the term of this patent is extended or adjusted under 35 U.S.C. 154(b) by 1985 days.

(21) Appl. No.: 11/914,310

(22) PCT Filed: May 10, 2006

(86) PCT No.: PCT/IB2006/001228
§ 371 (c)(1),
(2), (4) Date: Nov. 13, 2007

(87) PCT Pub. No.: WO2006/120551
PCT Pub. Date: Nov. 16, 2006

(65) Prior Publication Data
US 2008/0167666 A1 Jul. 10, 2008

(30) Foreign Application Priority Data
May 12, 2005 (FR) ..................................... 05 04745

(51) Int. Cl.
*A61B 17/064* (2006.01)
*A61F 2/44* (2006.01)
(Continued)

(52) U.S. Cl.
CPC ......... *A61B 17/0642* (2013.01); *A61B 17/0644* (2013.01); *A61B 17/0682* (2013.01);
(Continued)

(58) Field of Classification Search
USPC ........................................ 623/17.16; 606/75
See application file for complete search history.

(56) References Cited

U.S. PATENT DOCUMENTS

| 4,887,601 A | 12/1989 | Richards et al. |
| 5,993,476 A * | 11/1999 | Groiso .......................... 606/219 |

(Continued)

FOREIGN PATENT DOCUMENTS

| DE | 102 59 575 | 7/2004 |
| EP | 1 504 723 | 2/2005 |
| FR | 2 787 699 | 6/2000 |

*Primary Examiner* — Bruce E Snow
*Assistant Examiner* — Melissa Hoban
(74) *Attorney, Agent, or Firm* — Young & Thompson

(57) ABSTRACT

This equipment includes at least one U-shaped clip (1) whose lateral branches (10) have sections and widths such that they may be inserted in the vertebral bodies (100) of two vertebrae by impaction on the intermediate branch (11) of the clip (1), so as to rest along the cortical bones of the vertebral bodies, and whose intermediate branch (11) is deformable in such a way as to allow a reduction of the distance between the lateral branches (10); the intermediate branch, before implantation, has a length such that one of the lateral branches (10) may be positioned slightly above the cortical bone forming the plate of the subjacent vertebra while the other lateral branch (10) may be positioned slightly below the cortical bone forming the plate of the subjacent vertebra, and has, after deformation, a length such that the two lateral branches (10) may be brought closer to each other.

27 Claims, 4 Drawing Sheets

(51) Int. Cl.
*A61B 17/068* (2006.01)
*A61B 17/28* (2006.01)
*A61B 17/70* (2006.01)
*A61B 19/02* (2006.01)
*A61F 2/30* (2006.01)

(52) U.S. Cl.
CPC ............ *A61B 17/2833* (2013.01); *A61B 17/70* (2013.01); *A61B 19/0271* (2013.01); *A61B 2017/0688* (2013.01); *A61F 2/442* (2013.01); *A61F 2/4465* (2013.01); *A61F 2002/30576* (2013.01); *A61F 2002/30616* (2013.01); *A61F 2002/30841* (2013.01)

(56) References Cited

U.S. PATENT DOCUMENTS

| | | | |
|---|---|---|---|
| 6,325,805 B1 * | 12/2001 | Ogilvie et al. | 606/75 |
| 2002/0095155 A1 * | 7/2002 | Michelson | 606/61 |
| 2002/0107575 A1 * | 8/2002 | Metz-Stavenhagen | 623/17.16 |
| 2004/0002708 A1 * | 1/2004 | Ritland | 606/61 |
| 2005/0049600 A1 | 3/2005 | Groiso | |
| 2005/0273108 A1 | 12/2005 | Groiso | |

* cited by examiner

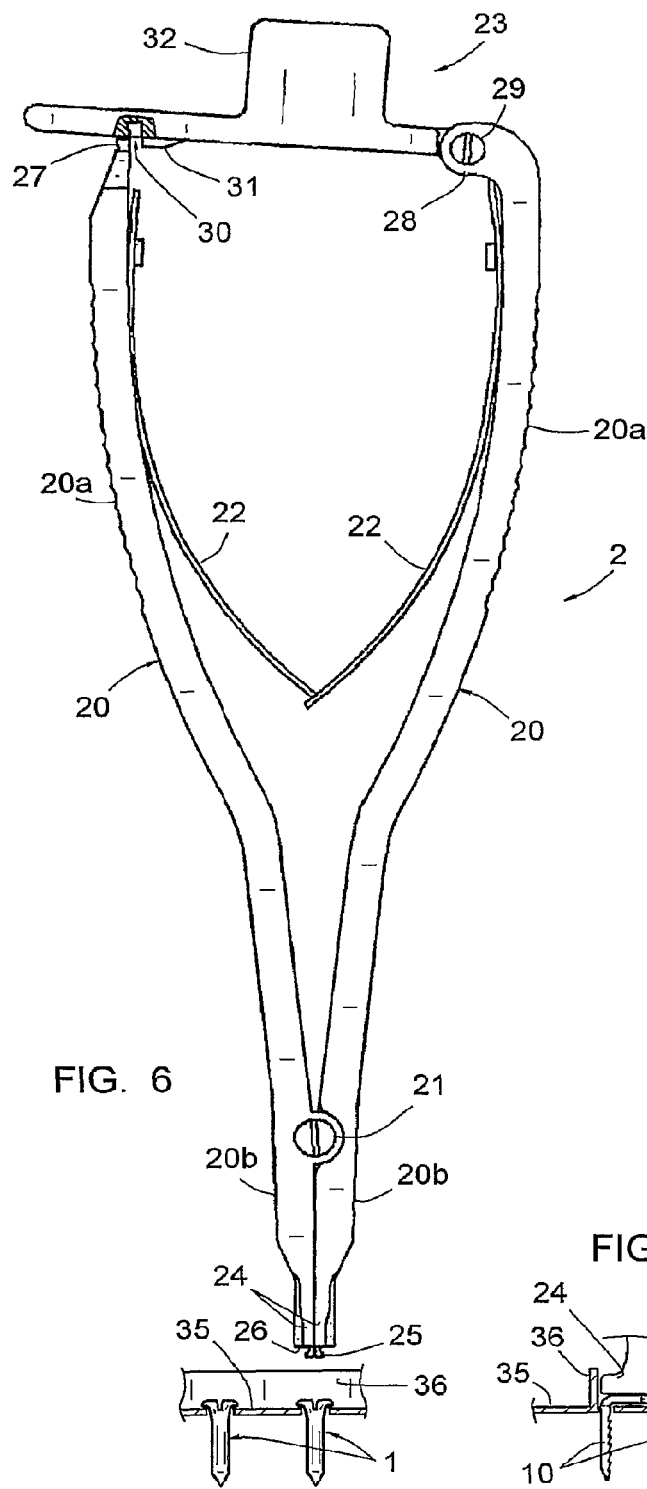
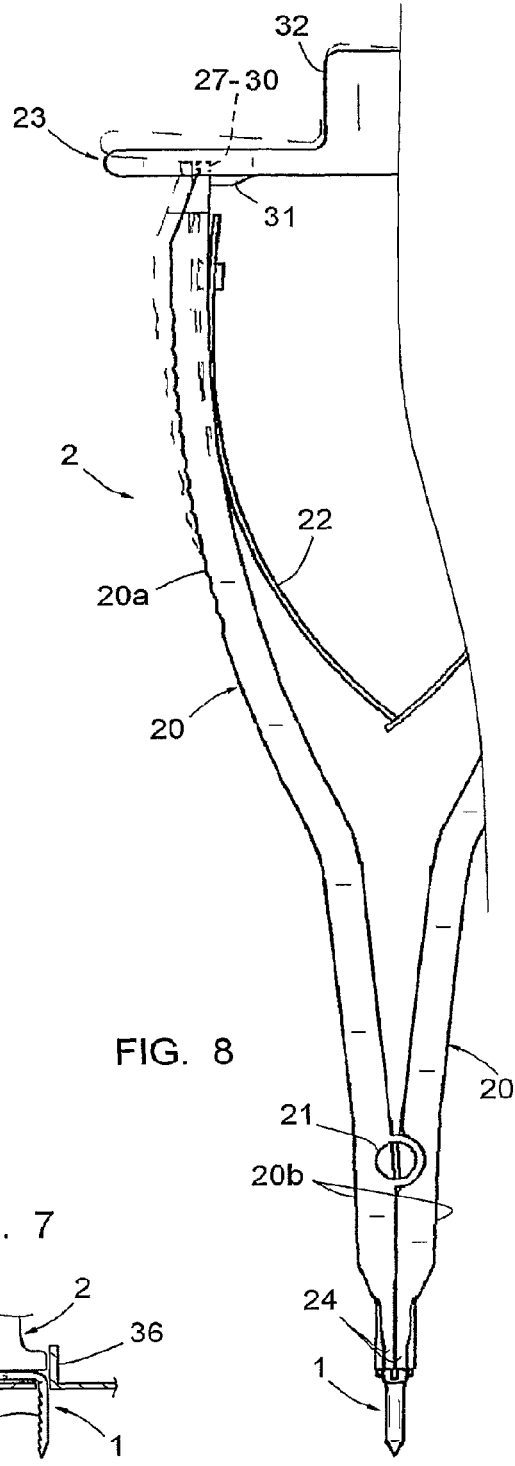
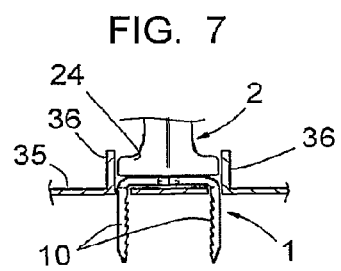
FIG. 6
FIG. 7
FIG. 8

VERTEBRAL OSTEOSYNTHESIS EQUIPMENT

BACKGROUND OF THE INVENTION

The present invention relates to vertebral osteosynthesis equipment. It also relates to the use of an osteosynthesis equipment for the treatment of vertebrae, particularly cervical vertebrae.

DESCRIPTION OF THE RELATED ART

Performing vertebral osteosynthesis, particularly cervical osteosynthesis, involves repositioning the vertebrae in a suitable manner with relation to each other, then completely immobilizing these vertebrae. This immobilization is achieved by inserting an intervertebral implant between two vertebrae and by immobilizing these vertebrae for the time that bone cell growth takes place. This intervertebral implant may only be a bone graft or may be formed by a rigid cage containing such a graft or containing cancelled bone fragments.

To prevent the risk of expulsion of the intervertebral implant, placing an osteosynthesis plate fixed to each of the two vertebrae by means of a screw on the anterior face of the vertebrae is common. Positioning such a plate and screw may be relatively long and complex, considering the small size of the implantation site, and may be dangerous. The rigidity of the plate is not particularly favorable for fusing vertebrae, and a significant risk of the screws unscrewing under the effect of repeated constraints exerted by the movements of the patient exists.

SUMMARY OF THE INVENTION

The objective of the present invention is to remedy these disadvantages.

In addition, for the fusing of the two vertebrae to take place, it is necessary that the vertebrae be tightly applied against the intervertebral implant. Some existing vertebral osteosynthesis plates have a significant disadvantage of not allowing this tight application to be securely achieved, in such a way that the vertebral fusion may not take place or may take place imperfectly.

Another objective of the present invention is to remedy this disadvantage.

The document No EP-A-1 504 723 discloses a clip for the treatment of long bones, having lateral branches and an intermediate branch. This intermediate branch is deformable in such a way as to allow a reduction of the distance between said lateral branches, so as to make the bone fragments come into contact one with each other and to immobilize these bone fragments in this manner.

An objective of the invention is to provide equipment specifically design for vertebral osteosynthesis, that is relatively simple and quick to position, with a slight flexibility that is favorable for fusing vertebrae.

Another objective of the invention is to provide equipment allowing a tight application of two vertebrae against an implant inserted between these vertebrae to be securely achieved.

An additional objective of the invention is to provide equipment comprising an instrument that notably facilitates vertebral osteosynthesis to be carried out.

To attain at least one of these objectives, the relevant equipment comprises, according to the invention, at least one U-shaped clip whose lateral branches have sections and widths such that they may be inserted in the vertebral bodies of the two vertebrae to be treated by impaction on the intermediate branch of the clip, so as to rest along the cortical bones of said vertebral bodies, and whose intermediate branch is deformable in such a way as to allow a reduction of the distance between said lateral branches; the intermediate branch, before implantation, has a length such that one of the lateral branches may be positioned slightly above the cortical bone forming the plate of the subjacent vertebra while the other lateral branch may be positioned slightly below the cortical bone forming the plate of the subjacent vertebra, and has, after deformation, a length such that the two lateral branches, and consequently the two vertebrae in which these lateral branches are implanted, may be brought closer to each other, said intermediate branch having a section such that it maintains the position the two treated vertebrae in a suitable manner with relation to each other.

Therefore, the clip is specifically design for vertebral osteosynthesis, particularly cervical vertebrae. It is impacted in such a way as to penetrate its lateral branches in the bodies of the two affected vertebrae, and then the intermediate branch is deformed in such a way as to bring these vertebrae to a suitable position and to maintain these vertebrae in said suitable position.

The lateral branches of the clip have a section allowing them to support this impaction and a width allowing them to rest against the cortical bones defining the vertebral plates in a stable manner, along these cortical bones, notwithstanding the constraints resulting from the deformation of the intermediate branch of the clip.

The clip of the equipment according to the invention is therefore particularly simple and quick to position and eliminates any insertion of screws in the vertebrae, and therefore all risk connected to possible unscrewing. Furthermore this clip presents a slight flexibility that the vertebral osteosynthesis plates do not present, that is favorable for stimulating the growth of bone cells in view of vertebrae fusing.

The equipment according to the invention advantageously comprises at least one intervertebral implant designed to be inserted between the vertebrae before positioning the clip.

Deformation of the intermediate branch of the clip allows, by bringing the two vertebrae closer to each other, a tight application of the vertebrae against this intervertebral implant, which allows bone fusion to be accomplished under the best conditions.

The equipment preferably comprises a plurality of clips having intermediate and/or lateral branches of different lengths.

The clip that is the most suitable for the patient treated may therefore be selected from among the series of clips that the equipment comprises.

Preferably, the intermediate branch of each clip is formed by two deformable branches extending one along the other, bent at the level of their median zones.

Antagonistic pressures may be exerted at the level of the bent zones of these branches in such a way as to deform the branches in order to increase the angulation of portions of said branches extending on both sides of said bent zones, and therefore reducing the length of the branches.

The clip thereby shaped may be made from a single band of material, in particular titanium, the median zone of this band being split to allow said deformable branches to be accommodated, and said band being folded to form said lateral branches and said intermediate branch.

Preferably, the opening separating said bent deformable branches extends beyond the areas connecting the lateral branches to the intermediate branch in such a way that each lateral branch itself presents a median slot, or a median feed slot at the level of its base.

This slot or feed slot promotes the deformation of the deformable branches at the level of said connection zones. Furthermore, it seems that this slot or feed slot allows, when deformation occurs, a slight tilting of the lateral branches in such a way that these lateral branches converge towards each other on their free extremities. This convergence is very favorable from the perspective of clip expulsion resistance.

The lateral branches of at least one clip advantageously comprise bone anchoring teeth arranged on the branches, preferably at their opposing sides.

The equipment according to the invention may comprise an instrument allowing a clip to be gripped as well as impacted, and then said intermediate branch of the clip to be deformed. According to the invention, this instrument comprises an anvil and two branches connected in a pivoting manner to each other, wherein each branch presents, at its working extremity, a stud appropriate for resting against the bent portion of a bent deformable branch of the clip, and a contact surface situated at the level of the base of the stud; the two branches of the instrument may be arranged first in a position of "gripping", in which the two studs can be inserted between the two deformable branches of the clip, near said bent portions, and in which said contact surfaces are brought along said intermediate branch of the clip; the two branches of the instrument may then be slightly pivoted to an "impacting" position, in which the two studs are slightly pressed against said bent portions and, by a slight elastic deformation of said intermediate branch of the clip, allow this intermediate branch to be maintained along said contact surfaces during the impaction operation; the two branches may then be pivoted additionally with relation to each other in such a way as to exert antagonistic pressures against said bent portions of said deformable branches and to therefore achieve deformation of these deformable branches.

The instrument is advantageously equipped with means allowing its branches to be immobilized in said "impacting" position.

Impaction may then be performed without having to manually hold the branches of the instrument in said "impacting" position during impaction.

Preferably, said means comprises elastic means for pivoting the branches one apart the other, a stud on one of the branches, a cross bar pivotally connected to the other branch, a cavity in the cross bar, appropriate for receiving said stud, and an abutment on the cross bar, the cavity being arranged in such a way as to be slightly offset with relation to the stud, in the normal position of the branches, and the abutment being immediately adjacent to the cavity, on the side of the cavity turned toward said other branch.

The equipment according to the invention may also comprise a support for presenting at least one clip, allowing said clip to be held such that a clip gripping instrument may easily grab this clip.

This presentation support may particularly be in the form of a plate with holes for receiving the lateral branches of at least one clip, and preferably a series of clips disposed in an orderly manner according to their dimensions.

The presentation support may be equipped with means for guiding an instrument allowing the gripping of a clip in order to ensure adequate positioning of this instrument with relation to this clip.

The invention also relates to the use of an osteosynthesis equipment comprising at least one U-shaped clip having lateral branches and an intermediate branch which is deformable in such a way as to allow a reduction of the distance between said lateral branches, for the treatment of vertebrae, particularly cervical vertebrae.

This clip can be used with an intervertebral implant inserted between the vertebrae before positioning the clip.

The invention will be clearly understood, and other characteristics and advantages of the invention will appear, with reference to the attached schematic drawing representing, by way of a non-limiting example, a preferred embodiment of the relevant equipment.

BRIEF DESCRIPTION OF THE DRAWING FIGURES

FIG. 6 is a view of the instrument before gripping a clip;

FIG. 7 is a partial view of the instrument at the time of gripping a clip;

FIG. 8 is a view of the instrument that is similar to FIG. 6, after gripping a clip;

FIGS. 1 to 5 represent a clip 1 utilized for osteosynthesis of two vertebrae, particularly cervical vertebrae.

DETAILED DESCRIPTION OF THE INVENTION

Figure 9:
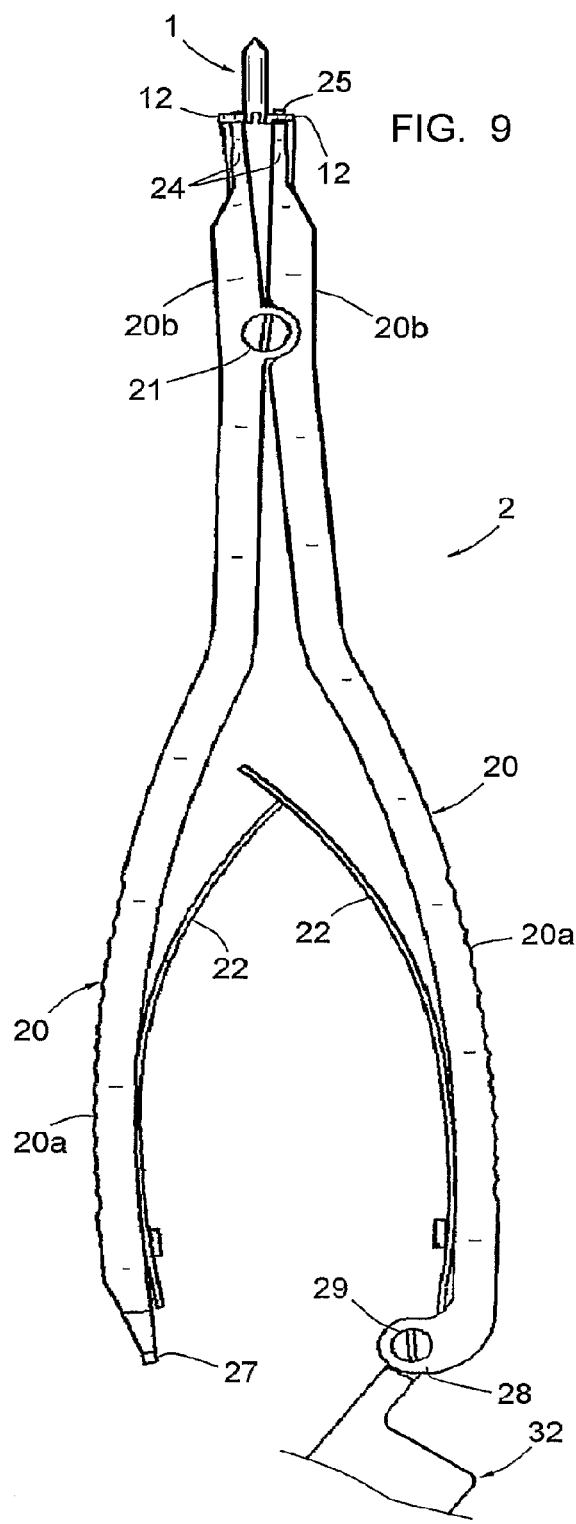
FIG. 9 is a view of the instrument that is similar to FIG. 6, after deformation of a clip.
Figure 10:
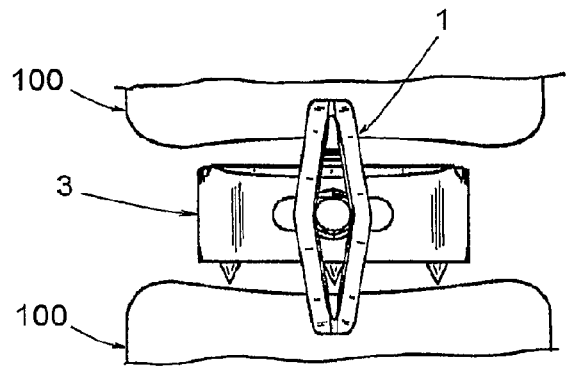
FIG. 10 is an end view of the clip, after impaction on two vertebrae and before deformation.
Figure 11:
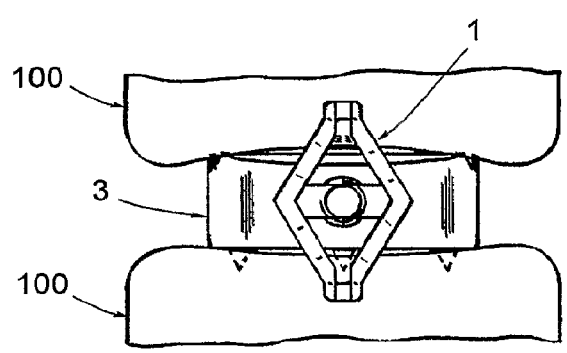
FIG. 11 is a view of the clip that is similar to FIG. 9, after deformation.
Figure 12:
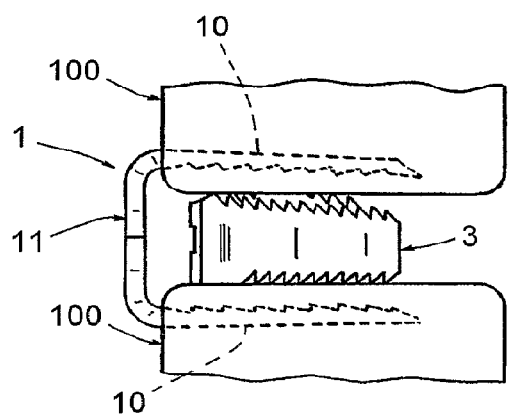
FIG. 12 is a side view of the clip after deformation.

This clip 1 is part of an item of vertebral osteosynthesis equipment, which also includes other clips 1 in different sizes, an instrument 2 shown in FIGS. 6 to 9, allowing gripping, impacting and deformation of each clip 1, and at least one intervertebral implant 3, more clearly seen in FIGS. 10 to 12.

The clip 1 has a U-shaped side view and, in the example represented, is obtained by double folding a band of titanium.

Its lateral branches 10 are designed to be inserted in the vertebral bodies 100 of two vertebrae to be treated, as shown in FIGS. 10 to 12, by impaction on the intermediate branch 11 of the clip, and are designed to rest against the cortical bones defining the plates of these vertebral bodies 100, along said plates. The lateral branches 10 have sections and widths provided as a result, particularly widths of 3 mm and thicknesses of 1.5 mm.

Different clips 1 from the series of clips that comprise the equipment have lateral branches 10 with different lengths, that may in particular range from 14 to 17 mm, such that the clip that is most suitable for the patient treated may be selected from among the series of clips that comprise this equipment.

As shown in FIGS. 1 to 5, the free extremities of the lateral branches 10 are cut in points to facilitate the insertion of these branches in the vertebral bodies 100. The faces of these branches 10 turned towards each other each comprise a series of bone anchoring teeth designed to rest against said cortical bones and to oppose the retraction of the branches 10 outside of the vertebral bodies 100.

The intermediate branch 11 of each clip 1 is formed by two deformable branches 12 extending one along the other, that are bent at the level of their median zones in such a way that this intermediate branch 11 has the form of a rhombus.

For the layout of these deformable branches 12, the titanium band from which a clip 1 is formed is slit longitudinally. Each band 12 may therefore in particular have a width and thickness on the order of 1.5 mm.

Different clips 1 from the series of clips that comprise the equipment have intermediate branches 11 with different lengths, that may in particular range from 15 to 20 mm, such that, here also, the clip that is most suitable for the patient treated may be selected from among the series of clips that comprise this equipment.

Figure 1:
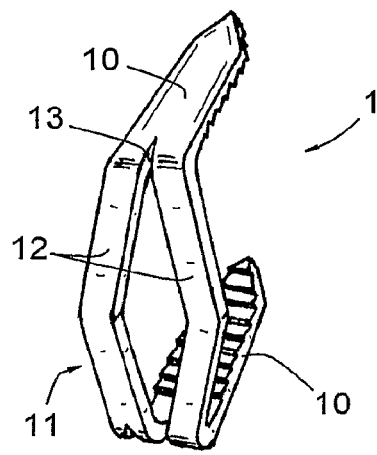
FIG. 1 is a perspective view of a clip that the figure comprises.
Figure 2:
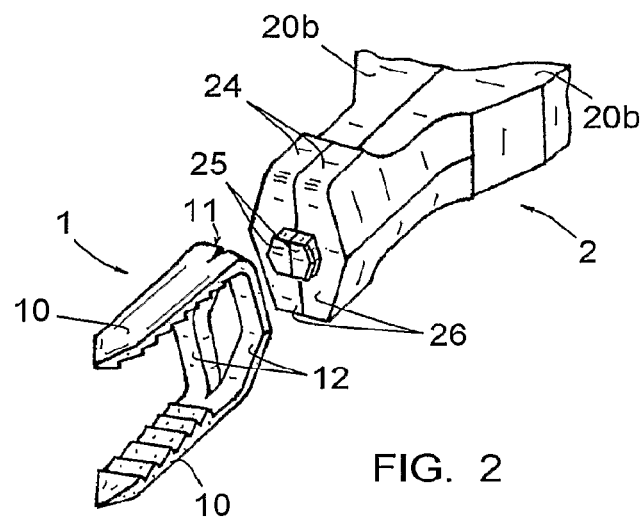
FIG. 2 is a perspective view of this clip from another angle, as well as the extremity of an instrument that comprises the equipment, allowing gripping, impacting and deformation of the clip.
Figure 3:
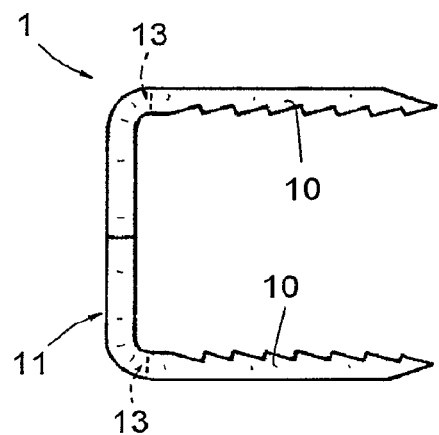
FIG. 3 is a side view of the clip.
Figure 4:
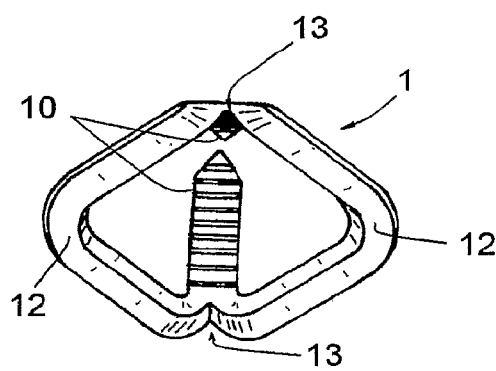
FIGS. 4 and 5 are perspective views of the clip from two different angles, after deformation.
Figure 5:
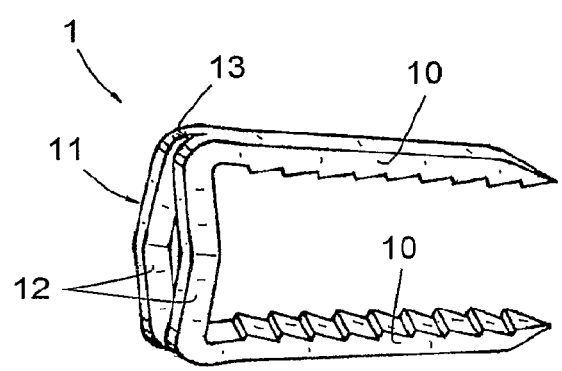

The intermediate branch 11 of each clip 1 is deformable between an un-deformed state, represented in FIGS. 1 to 3, and a deformed state, represented in FIGS. 4 and 5. In the non-deformed state, the intermediate branch 11 has a length such that one of the lateral branches 10 may be slightly positioned above the cortical bone forming the plate of the subjacent vertebral body 100 while the other lateral branch 10 may be positioned slightly below the cortical bone forming the subjacent vertebral body; in the deformed state, the bent portions of the deformable branches 12 are moved apart, and the intermediate branch 11 has a length such that the two lateral branches 10, and consequently the two vertebrae in which these branches are implanted, come closer together in order to tightly apply the vertebral plates of these vertebrae against the intervertebral implant 3, as appears by comparison of FIGS. 10 and 11.

The intermediate branch 11 have a section such that it maintains the position the two treated vertebrae in a suitable manner with relation to each other.

With reference to FIGS. 1 to 5, it would also appear that the slot allowing the branches 12 to be customized extends beyond the bent zones of the clip 1 by which the lateral branches 10 are connected to the intermediate branch 11. Each lateral branch 10 itself consequently presents a median slot 13 at the level of its base.

The instrument 2 comprises two branches 20 connected in a pivoting manner to each other by a pin 21, two curved elastic strips 22, and one cross bar 23 connected in a pivoting manner to one of the branches 20.

Each branch 20 comprises a rounded gripping part 20a and a rectilinear part 20b terminated, from the side opposite the rounded part 20a, by a work extremity.

The rectilinear parts 20b form flat inner faces which allow them, in the normal position of branches 20 imposed by the elastic recall of the strips 22 (see FIG. 6), to come in immediate proximity to each other.

As shown more particularly in FIG. 2, each work extremity comprises an enlarged head 24 extended by a gripping stud 25 and delimiting a contact surface 26 at the base of the stud 25.

Each stud 25 presents two exterior angular sides, wherein the angulation corresponds to the angulation of the inner edge of each branch 12, on both sides of the bent zone of each branch 12. The two studs 25 are, in addition, sized in such a way as to be able, when they are close to each other, to be engaged in the opening separating the two branches 12 and to rest against these branches 12 at the level of said bent zones.

Each stud 25 may comprise a slight flange projecting at the level of said angular sides, from the side of the free extremity of the stud, which allows gripping of the bent branch 12 to be ensured.

The contact surfaces 26 of the heads 24 form, when the work extremities are close to each other, a flat zone with a surface sufficient for receiving the whole intermediate branch 11 against the surfaces when the studs 25 are engaged between the branches 12 and that they rest against the latter in such a way as to ensure gripping of the clip 1.

At their extremities opposite from said work extremities, one of the branches 20 presents a stud 27 while the other branch 20 presents a curved portion 28 to which the cross bar 23 is connected.

The two elastic strips 22 are connected to the branches 20 by one of their extremities and rest against each other at their other extremities. The strips normally maintain the branches 20 in the position represented in FIG. 6, in which the two work extremities are in immediate proximity to each other.

The cross bar 23 is connected in a pivoting manner to the curved portion 28 by a pin 29, and has a length such that the cross bar extends beyond the branch 20 comprising the stud 27.

The cross bar comprises a cavity 30 appropriate for receiving this stud 27, an abutment 31 and an anvil 32.

The cavity 30 is arranged in such a way as to be slightly offset with relation to the stud 27, from the side of the pin 29, in the normal position of the branches 20, as appearing in FIG. 6.

The abutment 31 is immediately adjacent to the cavity 30, on the side of the cavity turned toward the pin 29.

The anvil 32 is situated roughly on the median axis of the instrument 2 and is designed to be struck to allow impaction of a clip 1.

As shown in FIGS. 6 and 7, a series of clips 1 is carried by a presentation plate 35, comprising holes for the passage of lateral branches 10 of the clips in such a way that the intermediate branches are against the upper face of this plate 35.

On both sides of each series of clips 1, the plate 35 comprises centering partitions 36, situated at a distance from each other that is slightly greater than the width of the heads 24 and the clips 1. These partitions 36 therefore allow centering of the instrument 2 with relation to a clip 1, and therefore the positioning of the studs 25 at the level of said bent zones of branches 12 to be ensured.

The intervertebral implant 3 may be of all known types: This may be only a bone graft or a rigid cage containing such a graft or fragments of cancellated bone.

Figure 13:
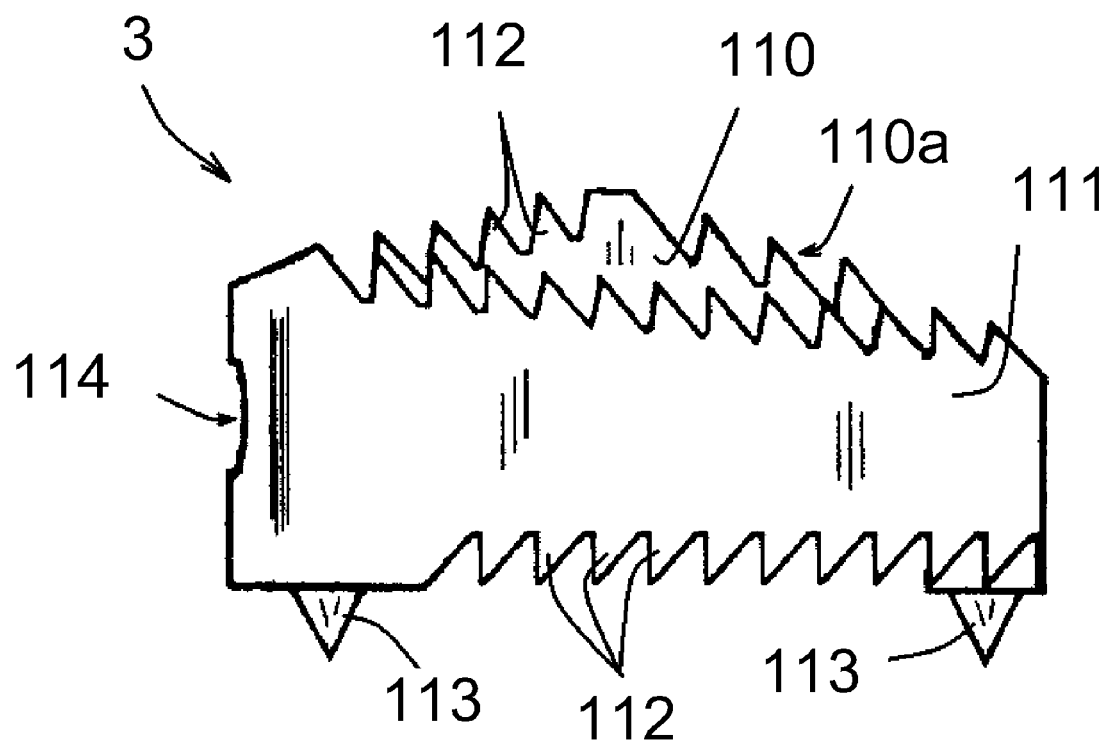
FIG. 13 is a side view of the implant.

In the example represented, and shown separately in FIG. 13, the implant 3 is formed by a rigid cage that is, for example, more or less D-shaped and comprises a median wall 110. The upper edge 110a of this median wall is rounded and projects beyond the upper edges of the walls 111 laterally delimiting the cage. The upper edge 110a of the median wall 110 and these upper edges of the walls 111 delimiting the cage comprise teeth 112 ensuring the maintenance of the implant 3 in position between the vertebrae. Furthermore, the cage presents lower pyramidal studs 113 appropriate for penetrating in subjacent vertebra and an elongated aperture 114 at one end that extends between the walls 111 laterally delimiting the cage.

In practice, the implant 3 is positioned between the vertebrae and the holes are arranged in the vertebral bodies 100 for reception of the lateral branches 10 of the selected clip 1.

While the stud 27 is not engaged in the cavity 30, the instrument 2 is presented between the partitions 36 of the plate 35, and then the studs 25 are engaged between the branches 12 of the selected clip 1. Manual pressure is then exerted on the parts 20a of the branches 20 in such a way as to cause the studs 25 to engage with the branches 12 and to therefore ensure firm gripping of the clip 1 by the instrument 2 (FIG. 7). Simultaneously, the stud 27 is brought to face the cavity 30; the cross bar 23 is then pivoted in such a way as to engage the stud 27 in the cavity 30 (FIG. 8), which locks the instrument 2 in this gripping position. The abutment 31 allows this position of engagement to be easily found and prevents any excessive pivoting of the branches 20 beyond the position sufficient for ensuring gripping of the clip 1. The elastic recall of the strips 22 ensures maintenance of the instrument in this position, this maintenance may be ensured by the layout of a projection on the stud 27, engaged in a reinforcement corresponding to cavity 30.

The clip 1 may then be presented facing the vertebrae by means of the instrument 2 and impaction of the latter may be performed by striking on the anvil 32.

Once impaction is performed, the cross bar 23 is disengaged from the stud 27 and is pivoted to clear the abutment 31 in order to authorize pivoting of the branches 20 in the direction of the clip 1 deformation (FIG. 9).

As shown in FIGS. 10 and 11, deformation of the intermediate branch 11 allows, by connecting the lateral branches 10 and therefore the two vertebrae to each other, a tight application of the vertebrae against the intervertebral implant 3. This tight application allows bone fusing to be accomplished under the best conditions.

Furthermore, as appears in FIGS. 5 and 12, the deformation of the branches 12 has the effect of achieving a slight tilting of the lateral branches 10 in such a way that these branches 10 converge towards each other from the side of their free extremities. This tilting results from the pivoting of the branches 12 at the level of the connection zones of the lateral branches 10 and the intermediate branch 11 as well as the presence of slots 13.

This convergence of the branches 10 is very favorable from the perspective of clip expulsion resistance.

As which appears from the previous, the invention provides an item of vertebral osteosynthesis equipment presenting the material advantages of:
being particularly simple and quick to position;
eliminating any insertion of screws in vertebrae, and therefore any risk connected to possible unscrewing;
utilizing a clip presenting a slight flexibility that is favorable for stimulating the growth of bone cells in view of fusing vertebrae;
allowing a tight application of the vertebrae against the intervertebral implant.

It goes without saying that the invention is not limited to the embodiment described above by way of example but that it extends to all embodiments covered by the attached claims.

The invention claimed is:

1. Vertebral osteosynthesis equipment, for achieving a bone fusion of two vertebrae, comprising:
   at least one U-shaped clip (1) having two lateral branches (10) and an intermediate branch (11) deformable in such a way as to allow a reduction of a distance between said lateral branches (10), each of said two lateral branches consisting of a single, median branch (10); and
   an intervertebral implant (3) that defines a cage comprising a median wall (110) and further walls (111) laterally delimiting the cage, the intervertebral implant (3) being adapted to be inserted between plates formed by vertebral bodies of vertebrae before positioning the at least one U-shaped clip (1), and wherein an upper edge (110a) of said median wall (110) is rounded and projects beyond upper edges of the further walls (111) laterally delimiting the cage,
   wherein the two lateral branches (10) have sections and widths such that the branches are configured to be inserted in the vertebral bodies (100) of two vertebrae to be treated by impaction on the intermediate branch (11) of the clip (1), so as to rest along the cortical bones of said vertebral bodies forming said plates,
   wherein the intermediate branch (11), before implantation, has a length allowing positioning one of the lateral branches (10) above the cortical bone forming the plate of the upper vertebra while the other lateral branch (10) is positioned below the cortical bone forming the plate of the lower vertebra, and has, after deformation, a length allowing the two lateral branches (10), and consequently the two vertebrae in which these lateral branches (10) are implanted, to be brought closer to each other, so as to bring the two vertebrae closer to each other, in a tight application against said intervertebral implant,
   wherein said intermediate branch (11) has a section such that the section maintains the position of the two treated vertebrae in relation to each other.

2. Equipment according to claim 1, wherein the at least one clip comprises a plurality of clips having lateral branches (10) of different lengths.

3. Equipment according to claim 2, wherein the intermediate branch (11) of each clip (1) is formed by two deformable branches (12) extending one along the other, bent at the level of their median zones, the two deformable branches providing flexibility to the clip.

4. Equipment according to claim 1, wherein the intermediate branch (11) of the at least one clip (1) is formed by two deformable branches (12) extending one along the other, bent at a level of their median zones, the two deformable branches providing flexibility to the clip.

5. Equipment according to claim 4, wherein the at least one clip (1) is made from a single band of material, the median zone of the band being split to allow said deformable branches (12) to be accommodated, and said band being folded to form said lateral branches (10) and said intermediate branch (11).

6. Equipment according to claim 5, wherein an opening separating said bent deformable branches (12) extends beyond areas connecting the lateral branches (10) to the intermediate branch (11) in such a way that each lateral branch (10) itself presents a median slot, or a median feed slot at the level of a base thereof, thus providing flexibility to the clip.

7. Equipment according to claim 5, further comprising:
   an instrument (2) comprising an anvil (32) and two branches (20) connected in a pivoting manner to each other,
   wherein each branch (20) presents, at its working extremity, a stud (25) appropriate for resting against the bent portion of a bent deformable branch (12) of the clip (1), and a contact surface (26) situated at the level of a base of the stud (25); the two branches (20) of the instrument (2) arrangeable first in a position of "gripping", in which the two studs (25) can be inserted between the two deformable branches (12) of the clip (1), near said bent portions, and in which said contact surfaces (26) are brought along said intermediate branch (11) of the clip (1); the two branches (20) of the instrument (2) may then be pivoted to an "impacting" position, in which the two studs (25) are pressed against said bent portions and, by a elastic deformation of said intermediate branch (11) of the clip (1), allow this intermediate branch (11) to be maintained along said contact surfaces (26) during the impaction operation; the two branches (20) may then be pivoted additionally with relation to each other in such a way as to exert antagonistic pressures against said bent portions of said deformable branches (12) and to therefore achieve deformation of these deformable branches (12).

8. Equipment according to claim 4, wherein an opening separating said bent deformable branches (12) extends beyond areas connecting the lateral branches (10) to the intermediate branch (11) in such a way that each lateral branch (10) itself presents a median slot, or a median feed slot at the level of a base thereof, thus providing flexibility to the clip.

9. Equipment according to claim 8, further comprising:
an instrument (2) comprising an anvil (32) and two branches (20) connected in a pivoting manner to each other,
wherein each branch (20) presents, at its working extremity, a stud (25) appropriate for resting against the bent portion of a bent deformable branch (12) of the clip (1), and a contact surface (26) situated at the level of a base of the stud (25); the two branches (20) of the instrument (2) arrangeable first in a position of "gripping", in which the two studs (25) can be inserted between the two deformable branches (12) of the clip (1), near said bent portions, and in which said contact surfaces (26) are brought along said intermediate branch (11) of the clip (1); the two branches (20) of the instrument (2) may then be pivoted to an "impacting" position, in which the two studs (25) are pressed against said bent portions and, by a elastic deformation of said intermediate branch (11) of the clip (1), allow this intermediate branch (11) to be maintained along said contact surfaces (26) during the impaction operation; the two branches (20) may then be pivoted additionally with relation to each other in such a way as to exert antagonistic pressures against said bent portions of said deformable branches (12) and to therefore achieve deformation of these deformable branches (12).

10. Equipment according to claim 4, further comprising:
an instrument (2) comprising an anvil (32) and two branches (20) connected in a pivoting manner to each other,
wherein each branch (20) presents, at its working extremity, a stud (25) appropriate for resting against the bent portion of a bent deformable branch (12) of the clip (1), and a contact surface (26) situated at the level of a base of the stud (25); the two branches (20) of the instrument (2) arrangeable first in a position of "gripping", in which the two studs (25) can be inserted between the two deformable branches (12) of the clip (1), near said bent portions, and in which said contact surfaces (26) are brought along said intermediate branch (11) of the clip (1); the two branches (20) of the instrument (2) may then be pivoted to an "impacting" position, in which the two studs (25) are pressed against said bent portions and, by a elastic deformation of said intermediate branch (11) of the clip (1), allow this intermediate branch (11) to be maintained along said contact surfaces (26) during the impaction operation; the two branches (20) may then be pivoted additionally with relation to each other in such a way as to exert antagonistic pressures against said bent portions of said deformable branches (12) and to therefore achieve deformation of these deformable branches (12).

11. Equipment according to claim 10 wherein the instrument (2) is equipped with parts (22, 23, 27, 30, 31) allowing its branches (20) to be immobilized in said "impacting" position.

12. Equipment according to claim 11, wherein said parts comprises elastic means (22) for pivoting the branches (20) one apart the other, a stud (27) on one of the branches (20), a cross bar (23) pivotally connected to the other branch (20), a cavity (30) in the cross bar (23), appropriate for receiving said stud (27), and an abutment (31) on the cross bar (23), the cavity (30) being arranged in such a way as to be offset with relation to the stud (27), in a normal position of the branches (20), and the abutment (31) being immediately adjacent to the cavity (30), on the side of the cavity turned toward said other branch (20).

13. Equipment according to claim 1, wherein the lateral branches (10) of the at least one clip (1) comprise bone anchoring teeth arranged on the branches (10) at their sides facing each other.

14. Equipment according to claim 1, further comprising a presentation support (35) for presenting at least one clip (1), allowing said clip (1) to be held such that a clip gripping instrument (2) may easily grab this clip (1).

15. Equipment according to claim 14, wherein the presentation support (35) is in the form of a plate with holes for receiving the lateral branches (10) of at least one clip (1).

16. Equipment according to claim 14 wherein the presentation support (35) is equipped with means (36) for guiding an instrument (2) allowing the gripping of one clip (1) in order to ensure adequate positioning of this instrument (2) with relation to the one clip (1).

17. Equipment according to claim 14, wherein the presentation support (35) in the form of a plate with holes for receiving the lateral branches (10) of a series of the clips (1) disposed in an orderly manner according to the clips' dimensions, wherein the presentation support is equipped with means (36) for guiding an instrument (2) allowing the gripping of a clip (1) in order to ensure adequate positioning of this instrument (2) with relation to this clip (1).

18. Equipment according to claim 1, wherein the at least one clip comprises a plurality of clips having intermediate branches (11) of different lengths.

19. Equipment according to claim 18, wherein the intermediate branch (11) of each clip (1) is formed by two deformable branches (12) extending one along the other, bent at the level of their median zones, the two deformable branches providing flexibility to the clip.

20. Equipment according to claim 1, wherein the lateral branches (10) have widths of 3 mm and thicknesses of 1.5 mm.

21. Equipment according to claim 1, wherein the upper edge of the median wall and said upper edges of the further walls laterally delimiting the cage comprise teeth ensuring the maintenance of the intervertebral implant (3) in position between the vertebrae.

22. Equipment according to claim 1, wherein the intervertebral implant presents lower pyramidal studs appropriate for penetrating in subjacent vertebra.

23. Vertebral osteosynthesis equipment, for achieving a bone fusion of two vertebrae, comprising:
a U-shaped clip (1) having two lateral branches (10) and an intermediate branch (11), the intermediate branch deformable to allow a reduction of a distance between said lateral branches (10), each of said two lateral branches consisting of a single, median branch (10); and
an intervertebral implant (3) that defines a cage comprising a median wall located between further walls laterally delimiting the cage, the intervertebral implant (3) being configured for insertion between plates formed by vertebral bodies of vertebrae before positioning the clip, wherein an upper edge of said median wall is rounded and projects beyond upper edges of the further walls laterally delimiting the cage, the upper edge of the median wall comprises teeth, and upper and lower edges of the further walls laterally delimiting the cage comprise teeth, the teeth of the upper edge of the median wall projecting beyond the teeth of the upper edge of the further walls laterally delimiting the cage comprise teeth, wherein the two lateral branches have sections and widths such that the branches are insertable, in the vertebral bodies of two vertebrae to be treated, by impaction on the intermediate branch of the clip, so as to rest along the cortical bones of said vertebral bodies forming said plates, wherein the intermediate branch (11), has
i) before implantation, a first length allowing one of the lateral branches to be positioned above the cortical bone forming the plate of the upper vertebra while the other lateral branch is positioned below the cortical bone forming the plate of the lower vertebra, and
ii) after deformation, a second length allowing the two lateral branches (10), and the two vertebrae in which these lateral branches (10) are implanted, to be brought closer to each other, so as to bring the two vertebrae closer to each other, in application against said intervertebral implant, and wherein said intermediate branch (11) has a section such that the section maintains the position of the two treated vertebrae in relation to each other.

24. Equipment according to claim 23, wherein the lateral branches (10) have widths of 3 mm and thicknesses of 1.5 mm.

25. Equipment according to claim 23, wherein the intervertebral implant (3) is D-shaped and comprises a median wall.

26. Equipment according to claim 23, wherein the intervertebral implant presents lower pyramidal studs appropriate for penetrating in subjacent vertebra.

27. A method for the osteosynthesis of vertebrae, including cervical vertebrae, comprising the steps of:
using vertebral osteosynthesis equipment comprising:
at least one U-shaped clip (1) having two lateral branches (10) and an intermediate branch (11) deformable in such a way as to allow a reduction of a distance between said lateral branches (10), each of said two lateral branches consisting of a single, median branch (10); and
an intervertebral implant (3) that defines a cage comprising a median wall (110) and further walls (111) laterally delimiting the cage, the intervertebral implant (3) being adapted to be inserted between plates formed by vertebral bodies of vertebrae before positioning the at least one U-shaped clip (1), and wherein an upper edge (110a) of said median wall (110) is rounded and projects beyond upper edges of the further walls (111) laterally delimiting the cage, wherein the two lateral branches (10) have sections and widths such that the branches are configured to be inserted in the vertebral bodies (100) of two vertebrae to be treated by impaction on the intermediate branch (11) of the clip (1), so as to rest along the cortical bones of said vertebral bodies forming said plates, wherein the intermediate branch (11), before implantation, has a length allowing positioning one of the lateral branches (10) above the cortical bone forming the plate of the upper vertebra while the other lateral branch (10) is positioned below the cortical bone forming the plate of the lower vertebra, and has, after deformation, a length allowing the two lateral branches (10), and consequently the two vertebrae in which these lateral branches (10) are implanted, to be brought closer to each other, so as to bring the two vertebrae closer to each other, in a tight application against said intervertebral implant, wherein said intermediate branch (11) has a section such that the section maintains the position of the two treated vertebrae in relation to each other;

positioning the intervertebral implant (3) between the plates formed by the bodies of the vertebrae;

arranged holes in the vertebral bodies (100) for reception of the lateral branches (10) of said clip (1), the hole arranged in the body of the upper vertebra being located above the critical bone forming the plate of this upper vertebra while the hole arranged in the body of the lower vertebra being located above the cortical bone forming the plate of this lower vertebra;

inserting said lateral branches (10) in said holes respectively and impacting on said intermediate branch (11) for inserting the lateral branches in said holes so as to rest along the cortical bones of said vertebral bodies forming said plates; and deforming said intermediate branch (11) so as to bring said two lateral branches (10), and consequently the two vertebrae in which these lateral branches (10) are implanted, closer to each other, in a tight application against said intervertebral implant.

* * * * *